United States Patent
Schüttler et al.

(10) Patent No.: US 10,172,560 B2
(45) Date of Patent: Jan. 8, 2019

(54) SENSOR MEANS FOR DETECTION OF BIOELECTRICAL SIGNALS

(71) Applicants: CorTec GmbH, Freiburg (DE); Albert-Ludwigs-Universität Freiburg, Freiburg (DE)

(72) Inventors: Martin Schüttler, Freiburg (DE); Jörn Rickert, Freiburg (DE); Christian Henle, Freiburg (DE); Tonio Ball, Freiburg (DE); Markus Raab, Freiburg (DE)

(73) Assignee: CorTec GmbH, Freiburg (DE)

(*) Notice: Subject to any disclaimer, the term of this patent is extended or adjusted under 35 U.S.C. 154(b) by 60 days.

(21) Appl. No.: 14/628,821

(22) Filed: Feb. 23, 2015

(65) Prior Publication Data
US 2015/0164425 A1  Jun. 18, 2015

Related U.S. Application Data

(63) Continuation of application No. PCT/EP2013/067531, filed on Aug. 23, 2013.

(30) Foreign Application Priority Data

Aug. 24, 2012 (DE) .................. 10 2012 107 838

(51) Int. Cl.
*A61B 5/00* (2006.01)
*A61B 5/0478* (2006.01)
*A61B 5/04* (2006.01)

(52) U.S. Cl.
CPC ........ *A61B 5/6868* (2013.01); *A61B 5/04001* (2013.01); *A61B 5/04004* (2013.01); *A61B 5/0478* (2013.01)

(58) Field of Classification Search
CPC ............ A61B 5/04001; A61B 5/04004; A61B 5/0478; A61B 5/6868
See application file for complete search history.

(56) References Cited

U.S. PATENT DOCUMENTS

| | | |
|---|---|---|
| 5,178,161 A | 1/1993 | Kovacs |
| 5,715,821 A | 2/1998 | Faupel |

(Continued)

FOREIGN PATENT DOCUMENTS

| | | | |
|---|---|---|---|
| DE | 20 2010 015 346 U1 | 3/2011 | |
| EP | 2 446 921 A1 | 5/2012 | |
| WO | WO 2009087486 A2 * | 7/2009 | ........... A61B 5/0476 |

OTHER PUBLICATIONS

Wang et al, Human Motor Cortical Activity Recorded with Micro-ECoG Electrodes During Individual Finger Movements, 2009, Conf Proc IEEE Eng Med Biol Soc., pp. 1-9.*

(Continued)

*Primary Examiner* — Etsub Berhanu
(74) *Attorney, Agent, or Firm* — Myers Wolin, LLC

(57) ABSTRACT

Sensor means for detection of bioelectrical signals, in particular, for implantation into or onto a brain wherein the sensor means comprises a first number of electrodes which can be coupled to a biological organism, in particular, to neural cells of a nervous system for tapping a first plurality of electrical potentials at the biological organism. According to the invention, the sensor means comprises means for providing an averaged electrical reference potential. The averaged electrical reference potential is formed from a plurality of detected electrical potential that are tapped at the biological organism.

4 Claims, 2 Drawing Sheets

(56) References Cited

U.S. PATENT DOCUMENTS

| | | | |
|---|---|---|---|
| 5,843,093 A * | 12/1998 | Howard, III | A61B 18/148 |
| | | | 600/372 |
| 6,597,954 B1 | 7/2003 | Pless | |
| 2009/0033333 A1 | 2/2009 | Gribova et al. | |
| 2011/0021943 A1* | 1/2011 | Lacour | A61N 1/0551 |
| | | | 600/546 |
| 2011/0230747 A1* | 9/2011 | Rogers | A61B 5/05 |
| | | | 600/377 |
| 2011/0295096 A1* | 12/2011 | Bibian | A61B 5/0478 |
| | | | 600/372 |
| 2012/0123232 A1 | 5/2012 | Najarian | |
| 2012/0257339 A1* | 10/2012 | Leyde | H03F 3/45475 |
| | | | 361/679.01 |

OTHER PUBLICATIONS

Shaw et al, A simple and effective process for noise reduction of multichannel cortical field potential recordings in freely moving rats, 2003, Journal of Neuroscience Methods, 124(2): 167-74.*

International Search Report, dated Dec. 13, 2013, for International Application No. PCT/EP2013/067531.

Office Communication Examination issued for European Patent Application No. 13 774 080.9 dated Nov. 18, 2016 with an English translation.

* cited by examiner

SENSOR MEANS FOR DETECTION OF BIOELECTRICAL SIGNALS

CROSS REFERENCE TO RELATED APPLICATIONS

This application is a continuation of International Application No. PCT/EP2013/067531, filed Aug. 23, 2013, which claims priority to German Application No. 10 2012 107 838.6, filed Aug. 24, 2012, the contents of each of which are incorporated by reference herein.

FIELD OF THE INVENTION

The invention relates to a sensor means for detection of bioelectrical signals, in particular, for implantation into or onto a brain, in particular, a human brain.

BACKGROUND OF THE INVENTION AND PRIOR ART

It is known to detect or record bioelectrical signals, for example, of a human brain, by means of a medicated implant. For detection of bioelectrical signals at least two electrical contacts or electrodes are necessary which are connected to the biological organism or which are coupled to the biological organism. With one of the two contacts, the bioelectrical signal is detected in form of an electrical potential change. A detection of an electrical potential change also is called "derivation of a signal". The other one of the two contacts is coupled to a static, if possible non-changing, electrical potential within the same organism such that this contact provides a so-called reference potential. The reference potential between the two electrical contacts or the change of this potential difference forms the bioelectrical signal to be detected. This type of detection or derivation is called monopolar derivation. The monopolar derivation is used if the bioelectrical signal is only to be detected at a single contact.

As alternative for the monopolar derivation, also the so-called bipolar derivation is known. With respect to the bipolar derivation, the reference electrode which provides a reference potential for the monopolar derivation, may also be arranged in the electrically active area of the biological organism. As an alternative to this, it is known to arrange the reference electrode as arranged for the monopolar derivation in the electrically passive area of the biological organism, and to provide a third electrical contact which is arranged in the electrically active area. With respect to the bipolar derivation with two electrical contacts and a reference electrode, the potential difference between the two electrical contacts or between the two electrical contacts and the reference electrode is measured.

The present invention relates to a monopolar derivation of bioelectrical signals.

The electrical contact which is arranged in the electrically active area of the biological organism in the following is referred to as derivation contact or derivation electrode. The electrical contact which provides a reference signal or a reference potential in the following is referred to as reference contact or reference electrode.

The monopolar derivation known from prior art, however, is disadvantageous because the arrangement of the derivation electrode and reference electrode with respect to each other should meet two requirements which, however, are conflicting to a large extent.

According to a first requirement, the derivation electrode and the reference electrode should be placed as close as possible with respect to each other.

A distance as close as possible or a minimal distance between the derivation electrode and the reference electrode is accompanied by low electrical impedance between the two electrodes because lower volumes of biological tissue between the two contacts represent a lower electrical resistance than large volumes. Proportionally to the electrical resistance between the two electrodes, the amplitude of a thermal noise emerges which compromises or affects the quality of the bioelectrical signal to be derived or to be detected negatively.

Moreover, a smaller distance between derivation electrode and reference electrode reduces the surface of a virtual conductor loop which is created by the electrode feed lines and the current path through the biological tissue (between the two electrode contacts). The larger the surface of such a conductor loop is, the larger the electrical voltage between the derivation electrode and the reference electrode will be which is created by inductance when an alternating magnetic field passes through the conductor loop. This electrical voltage superposes the bioelectrical signal to be detected, and in the worst case, it may completely mask or bring the electronical amplifier into the saturation region preventing a possibly necessary amplification of the weak bioelectrical signal. Sources for an alternating magnetic field, for example, may be a mains current of 50 Hz, an anti-theft system in department stores, radio frequency identification systems (RFID), or the like.

According to a second requirement, the derivation electrode and the reference electrode should be placed as far as possible away from each other.

By a large geometric distance between the derivation electrode and the reference electrode it may be guaranteed that the electrical potential of the reference electrode is independent of the source of the bioelectrical signal in the vicinity of the derivation electrode. Thereby, the potential difference between the derivation electrode and the reference electrode can be maximized such that the bioelectrical signal can be detected and evaluated better, and can be distinguished more easily from interferences.

With respect to a reference electrode which is arranged close to the derivation electrode, the characteristics of the signal derivation corresponds to a bipolar derivation such that this approach leads to a mixing of the bioelectrical signals which are derived from the two contacts, and in the worst case, it prevents a detection of a bioelectrical event. Because, if both contacts (reference electrode and derivation electrode) simultaneously detect an identical or nearly identical signal, the electrical potential difference to be amplified is zero or nearly zero.

Therefore, in prior art the reference electrode is placed at some distance away from the derivation electrode in order to achieve a good signal quality and a good local selectivity which, however, requires that the surroundings is specifically interference free which in most cases is only possible under laboratory conditions.

Therefore, it is an object of the present invention to provide solutions for derivation or for detection of bioelectrical signals, in particular, bioelectrical signals of a brain which at least partially avoid the disadvantages from prior art, and which allow for a detection of bioelectrical signals independently of the arrangement of the electrodes with respect to each other.

SUMMARY

This object is solved according to the invention by a sensor means for detection of bioelectrical signals, in particular, for implantation into or onto a brain, according to the independent claim. Preferred embodiments and further developments of the invention are defined in the dependent claims.

Accordingly, a sensor means for detection of bioelectrical signals is provided, in particular, for implantation into or onto a brain wherein the sensor means comprises a first plurality of electrodes which can be coupled to a biological organism, in particular, to neural cells of a nervous system for tapping a first plurality of electrical potentials at the biological organism. According to the invention, the sensor means comprises means for providing an averaged electrical reference potential. The averaged electrical reference potential is formed from several detected electrical potentials which are tapped at the biological organism.

Thereby, it is guaranteed that the electrical potential difference to be amplified is not zero, and also with adverse surrounding conditions, a bioelectrical event can be detected reliably. Contrary to the monopolar derivation known from prior art, the sensor means according to the present invention is distinguished by a reduced noise and large signal amplitudes which leads to an improved signal quality. A further advantage is the reduced sensitivity to interferences, for example, with respect to electromagnetic interferences which leads to an improved reliability of the sensor means according to the invention.

It is advantageous if the means for providing an averaged electrical reference potential are integrated into the sensor means, and may be implanted together with the sensor means.

Thereby, the information volume to be transmitted to a processing unit exterior to the body can be reduced substantially because now, an averaged electrical reference potential has to be transmitted, and not several single reference potentials which would have to be averaged by the processing unit exterior to the body.

The sensor means may comprise a first plurality of amplifiers, in particular, differential amplifiers, wherein a first input of each differential amplifier is connected respectively to an electrode of the first plurality of electrodes, and a second input to the means for providing an averaged electrical reference potential.

Thereby, a change of the potential difference between an electrode and the averaged reference potential can be amplified to a dimension which electrically is easy to handle.

In an embodiment of the invention, the means for providing an averaged electrical reference potential may comprise a second plurality of reference electrodes which are connected to each other galvanically, and which may be coupled to the biological organism.

The reference electrode which is formed by the second plurality of reference electrodes may thereby be arranged immediately adjacent to the derivation electrodes such that the advantages of two electrodes being placed as close as possible with respect to each other may be exploited completely. By forming the reference electrode from a plurality of reference electrodes it is avoided that the derivation characteristics correspond to a bipolar derivation. The second plurality of reference electrodes may be arranged locally close distributed around a derivation electrode.

Each reference electrode of the second plurality of reference electrodes detects an electrical potential in its immediate vicinity. By galvanically or electrically connecting the single reference electrodes to the second plurality of reference electrodes, the single detected potentials are averaged. Thereby, the reference potential is rendered insensitive to local bioelectrical signals wherein the reference electrode or the second plurality of reference electrodes, however, may be placed into immediate vicinity to the first plurality of electrodes or to the derivation electrodes.

The potential difference to be amplified between the averaged electrical reference potential and an electrical potential at the derivation electrode, thereby, is large and the influence of interferences, for example, thermal noise and magnetically induced voltage can be reduced or minimized.

The galvanic connections between the reference electrodes of the second plurality of reference electrodes may comprise a mechanically elastic connection. Thereby, it is prevented that a mechanical extension of an implant on which the electrodes and the conductor paths are arranged lead to breakage of the conductor paths.

It has been found to be advantageous if the galvanic connections between the reference electrodes comprise meandering conductor paths.

In a preferred embodiment of the invention, the reference electrodes are arranged with respect to the electrodes (derivation electrodes) such that the distances between a reference electrode and the immediately adjacent electrodes basically are the same.

In an embodiment of the invention, the first plurality of electrodes may be larger than e second plurality of reference electrodes.

In an embodiment of the invention, the means for providing an averaged electrical reference potential may comprise a first plurality of first electrical resistances wherein each electrode is connected respectively to one of the first electrical resistances, and the first electrical resistances in turn are connected to each other in a node which provides the averaged electrical reference potential.

The electrical reference potential is created by the electrical potentials detected at the derivation electrodes such that no reference electrodes have to be provided for providing the reference potential. Thereby, all electrodes can be used for derivation of bioelectrical signals.

The node may be connected to the ground potential of the supply voltage of the derivation amplifier via a second electrical resistance. Thereby, it can be guaranteed that the operating range of the amplifier or the derivation amplifier is close to the reference potential. Alternatively, the node may also be connected to another mass via the second electrical resistance, for example, to housing mass or to the mass of the circuit board.

The first electrical resistances which are connected to the first plurality of electrodes may be configured highly resistive.

In an embodiment of the invention, the means for providing an averaged electrical reference potential may comprise an electrode wherein the averaged electrical reference potential is famed by an average over time of the electrical potential detected at this electrode.

BRIEF DESCRIPTION OF THE DRAWINGS

Further details and features of the invention as well as concrete embodiments of the invention can be derived from the following description in connection with the drawing in which.

DETAILED DESCRIPTION OF THE PREFERRED EMBODIMENTS

Figure 1:
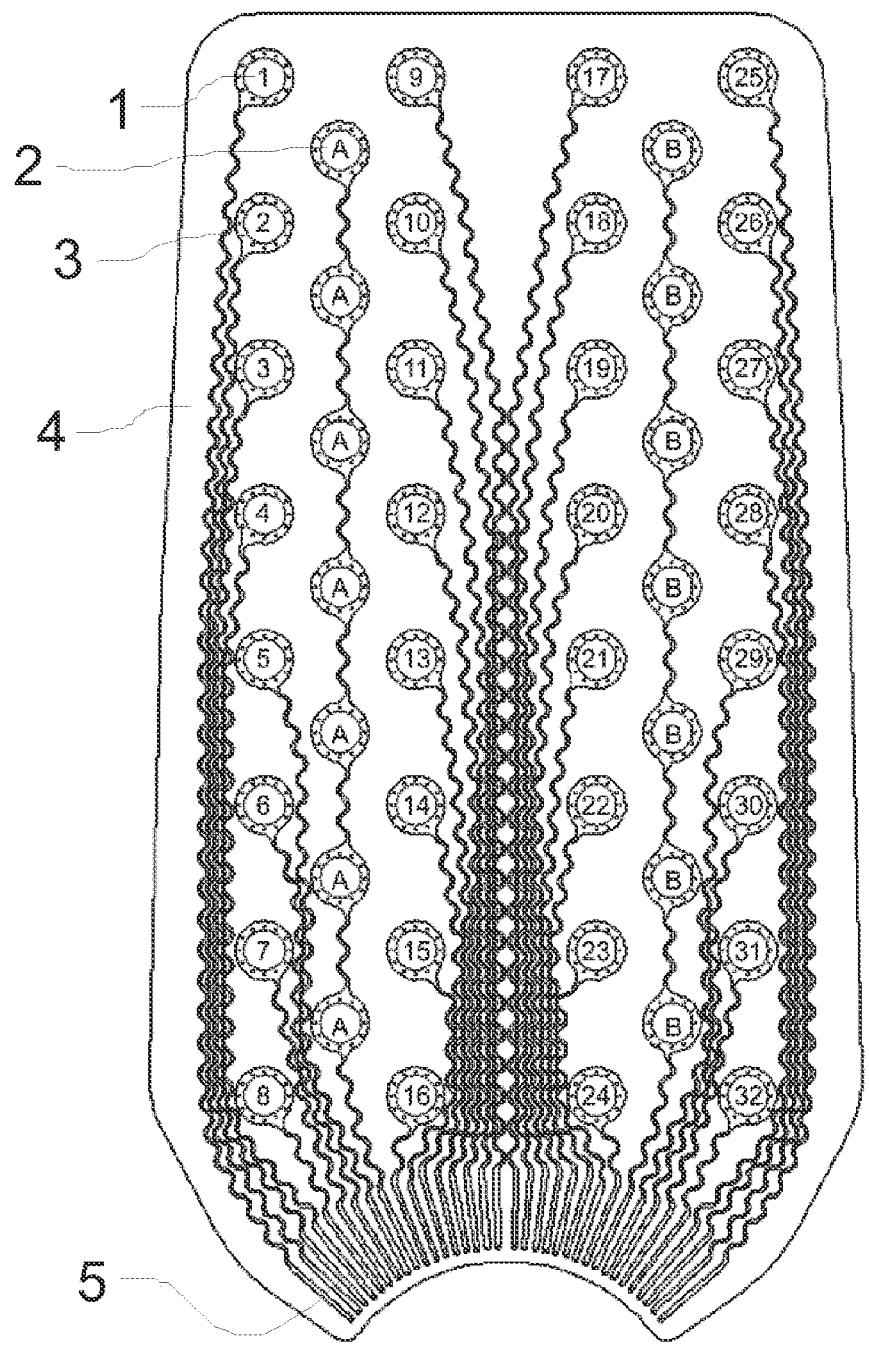
FIG. 1 shows an embodiment of the invention in the form of an electrode pad which can be implanted into or onto a brain, and on which a plurality of derivation electrodes and a plurality of reference electrodes are applied.

FIG. 1 shows a first embodiment of the invention in the form of an electrode pad on which a plurality of electrodes or derivation electrodes 1 (the derivation electrodes here are numbered consecutively from 1 to 32) and two reference electrodes 2 (the reference electrodes are indicated by the letters A and B) are arranged.

The derivation electrodes 1 are respectively connected to conductor paths 3 to terminals which are located in the terminal area 5 of the electrode pad. According to FIG. 1, two reference electrodes 2 (A and B) are arranged on the electrode pad wherein each reference electrode is formed from seven single contacts which are connected to each other via conductor paths.

The derivation electrodes 1, the reference electrodes 2, the conductor paths of the derivation electrodes 1, and the conductor paths connecting the single contacts of the reference electrodes are embedded into the electrically isolating substrate of the electrode pad. The electrically isolating substrate has apertures in the areas of the derivation electrodes or the single contacts of the reference electrodes such that the derivation electrodes and the single contacts of the reference electrodes can be coupled to a biological organism, for example, to the neural cells of a nervous system.

In the embodiment shown here, the conductor paths are configured in a meandering manner such that a mechanical extension of the electrode pad is possible without the danger of breakage of the conductor paths.

The single contacts of the reference electrode 2 are arranged between the derivation electrodes 1 such that they always basically have a same distance to the derivation electrodes 1. By the galvanic connection of the single contacts of a reference electrode 2, the potentials detected at the individual single contacts are averaged such that an averaged reference potential is provided at the terminal of a reference electrode. Hereby, it is advantageous that now only one terminal contact has to be provided in order to, for example, transmit the averaged reference potential to a processing unit exterior of the body. The number of signals to be transmitted to a processing unit exterior of the body, thus, can be decreased substantially. The averaged reference potential thus provided may be used in order to detect an electrical potential difference between the averaged reference potential and an electrical potential detected at a derivation electrode 1, and to amplify these, if needed, by means of an amplifier, for example, a differential amplifier.

Because the single contacts of the reference electrodes 2 respectively have a different distance to each derivation electrode 1, it is guaranteed that the reference electrode formed by the single contacts is insensitive to local bioelectrical signals in the area of an individual derivation electrode. As can be seen in FIG. 1, it nevertheless is guaranteed that a single contact of a reference electrode 2 is arranged at each derivation electrode 1 in immediate vicinity such that the previously mentioned requirement according to which a derivation electrode and a reference electrode should be located as close as possible to each other, is fulfilled. Because each single contact of a reference electrode 2 has a different distance to a certain derivation electrode, the second requirement mentioned above according to which a reference electrode 2 and a derivation electrode should be placed from each other as far as possible is, however, fulfilled for the single contact of the reference electrode 2 being spaced apart from the derivation electrode the most.

Of course, also variants of an arrangement of derivation electrodes and reference electrodes on an electrode pad other than the column shaped arrangement shown in FIG. 1 are possible.

Also, more or less than the 32 derivation electrodes shown in FIG. 1 and more or less than the seven single contacts of the reference electrodes shown in FIG. 1 or also more than two reference electrodes may be provided.

Figure 2:
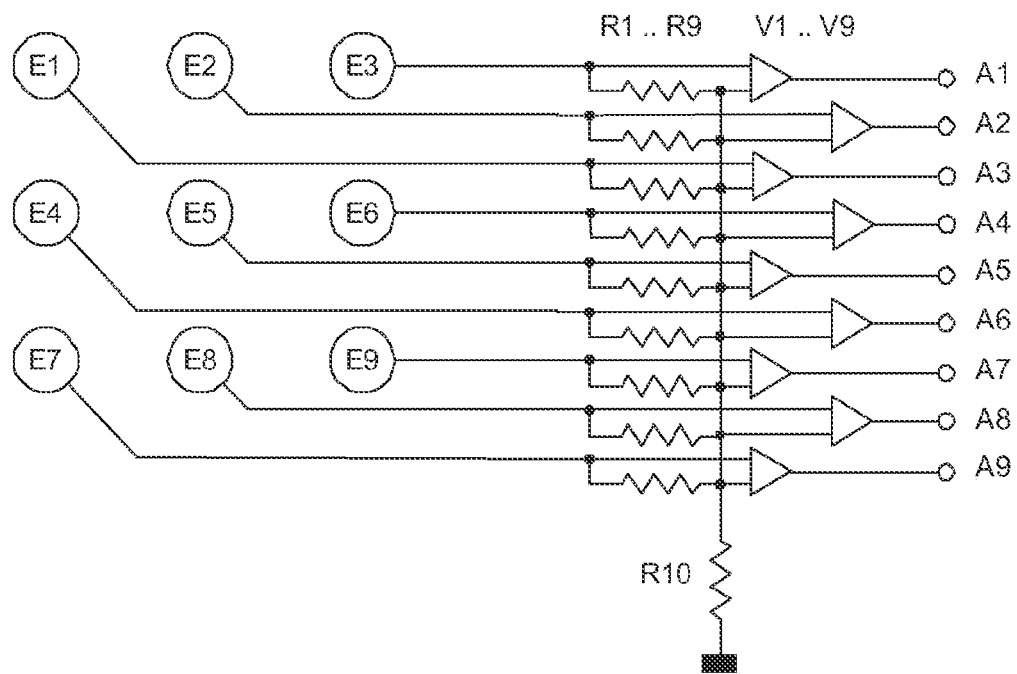
FIG. 2 shows an alternative embodiment of a sensor means according to the invention according to which no separate reference electrodes are necessary.

FIG. 2 shows a further embodiment of a sensor means according to the invention for detection of bioelectrical signals, in particular, for implantation into or onto a brain.

In FIG. 2, a nine-channel-electrode array is shown which has nine derivation electrodes E1 to E9. Further, the sensor means shown in FIG. 2 has an amplifier or differential amplifier V1 to V9 for each channel. The derivation electrodes E1 to E9 respectively are coupled directly via a contact to a first input of respectively one differential amplifier V1 to V9. Further, all derivation electrodes E1 to E9 are respectively connected to each other via a highly resistive resistance R1 to R9. For example, resistances of 10 MΩ may be provided.

The connection point or node of the electrical resistances R1 to R9 forms the reference of all differential amplifiers V1 to V9, i.e., at the node of the electrical resistances R1 to R9, a reference potential is tapped for the differential amplifier. From an electrical point of view, the electrical potential tapped at the node of the electrical resistances R1 to R9 corresponds to the average potential of all derivation electrodes E1 to E9.

In order to guarantee that the operation range of the amplifiers V1 to V9 lies close to the reference potential, the node or connection point is connected to the ground potential of the supply voltage of the differential amplifiers V1 to V9 via a second electrical resistance which, for example, lies in the region of a few kΩ. Alternatively, the second electrical resistance may also be connected to another mass.

After amplification of the respective potential differences, the signals detected at the outputs A1 to A9 of the differential amplifiers by the derivation electrodes E1 to E9 are available in amplified form.

The embodiment according to FIG. 2 has the advantage that all electrodes of the sensor means can be used for electrical derivation or for detection of bioelectrical signals. No individual or additional reference electrodes have to be provided because the derivation electrodes E1 to E9 are used in combination with the electrical resistances R1 to R9 also as reference electrodes wherein the derivation electrodes E1 to E9 are interconnected via the resistances R1 to R9 to a single reference electrode. Thereby, the area available on an electrode pad may be used optimally because instead of separate reference electrodes or electrode contacts of a reference electrode, additional derivation electrodes may be arranged.

The sensor means shown here is provided, in particular, in order to be implanted into or onto a brain, and to be coupled there to neural cells of a nervous system.

REFERENCE NUMERALS 1 electrodes or derivation electrodes 1 to 32
2 reference electrodes A and B
3 conductor paths
4 electrically isolating substrate
5 terminal area E1 to E9 electrodes or derivation electrodes
R1 to R9 electrical resistances
R10 electrical resistance to ground potential of the amplifier
V1 to V9 amplifier (differential amplifier)
A1 to A9 terminals (electrode signals after amplification)

What is claimed is:

1. A sensor means for detection of bioelectrical signals for implantation into a brain wherein the sensor means comprises a pad with a first plurality of electrodes which can be coupled to neural cells of a nervous system of a biological organism, for tapping a first plurality of electrical potentials at the biological organism, characterized in that:
the sensor means comprises means for providing an averaged electrical reference potential,
wherein the means for providing an averaged electrical reference potential comprises a second plurality of reference electrodes arranged on the pad, the reference electrodes being connected to each other galvanically via conductor paths arranged on the pad such that an average potential is provided at a terminal of a reference electrode, and can be coupled to the biological organism, and
wherein the reference electrodes are arranged with respect to the electrodes of the first plurality of electrodes such that respective distances between a reference electrode and immediately adjacent electrodes of the first plurality of electrodes are the same.

2. The sensor means of claim 1, wherein the galvanic connections comprise mechanically extendable connections.

3. The sensor means of claim 1, wherein the galvanic connections comprise meandering conductor paths.

4. The sensor means of claim 1, wherein the first plurality is larger than the second plurality.

* * * * *